United States Patent [19]

Standridge

[11] 4,125,538
[45] Nov. 14, 1978

[54] SUBSTITUTED 5-PHENYL-2,3,4,5-TETRAHYDRO-1,4-BENZOXAZEPINES

[75] Inventor: Robert T. Standridge, Cazenovia, N.Y.

[73] Assignee: Bristol-Myers Company, New York, N.Y.

[21] Appl. No.: 765,513

[22] Filed: Feb. 4, 1977

[51] Int. Cl.$^2$ .................. C07D 413/06; A61K 31/55; C07D 267/14
[52] U.S. Cl. .................... 260/326.5 CA; 260/326.5 S; 260/333; 424/274; 424/244
[58] Field of Search ........ 260/326.5 CA, 333, 326.5 S

[56] References Cited

U.S. PATENT DOCUMENTS

| | | | |
|---|---|---|---|
| 2,807,628 | 9/1957 | Belleau | 260/333 |
| 3,127,409 | 3/1964 | Yale et al. | 260/326.5 CA |
| 3,346,565 | 10/1967 | Testa et al. | 260/239.3 |
| 3,676,460 | 7/1972 | Hirohashi et al. | 260/333 |
| 3,686,217 | 8/1972 | Schenker | 260/333 |
| 3,794,639 | 2/1974 | Krapcho et al. | 260/239.3 B |

FOREIGN PATENT DOCUMENTS

| | | |
|---|---|---|
| 764,865 | 9/1971 | Belgium. |
| 2,100,654 | 7/1971 | Fed. Rep. of Germany. |
| 67/05136 | 1/1968 | South Africa. |

OTHER PUBLICATIONS

H. A. Luts, Journal of Pharmaceutical Sciences 58, 1460–1463, (1969).
G. N. Walker et al., J. of Organic Chemistry 36, 305–308 (1971).
Hirohashi et al., Chemical Abstracts 73, 120697h (1970).
D. Huckle et al., J. of the Chemical Society, 1137–1141 (1965).
J. Muelberger et al., Chemical Abstracts 75, 129856m (1971).
J. Muelberger et al., Chemical Abstracts, vol. 76, 25321n, (1972).

*Primary Examiner*—Jose Tovar
*Attorney, Agent, or Firm*—Richard R. Lloyd

[57] ABSTRACT

Substituted 5-phenyl-2,3,4,5-tetrahydro-1,4-benzoxazepines of the formula

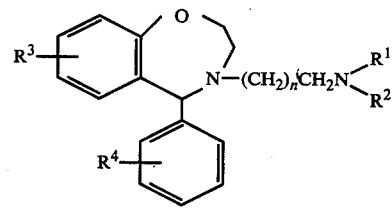

wherein $R^1$ and $R^2$ are each methyl or, when taken together with the nitrogen to which they are attached, represent pyrrolidino, $R^3$ and $R^4$ are the same or different and represent hydrogen, chloro, fluoro, bromo, iodo, nitro, (lower)alkyl, trifluoromethyl, (lower)alkoxy, trifluoromethoxy or (lower)alkylthio, and n is an integer from 1 to 4, and their nontoxic pharmaceutically acceptable acid addition salts, are valuable analgesic and/or antitussive agents.

14 Claims, No Drawings

SUBSTITUTED 5-PHENYL-2,3,4,5-TETRAHYDRO-1,4-BENZOXAZEPINES

BACKGROUND OF THE INVENTION

1. Field of the Invention

This invention relates to 5-phenyl-2,3,4,5-tetrahydro-1,4-benzoxazepines containing an ω-(dimethylamino)alkyl or ω-(pyrrolidino)alkyl substituent on the ring nitrogen, and optionally containing substituents in the 5-phenyl ring and/or the 6-, 7-, 8- or 9-position, and their nontoxic pharmaceutically acceptable acid addition salts, which are useful as analgesic and/or antitussive agents.

2. Description of the Prior Art

In the Journal of Pharmaceutical Sciences, 58, 1460–1463 (1969), H. A. Luts discloses substituted 1,4-benzoxazepines of the formulae

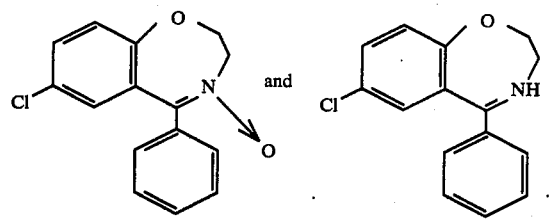

No specific utility is given for the compounds, it is merely stated that they were prepared "in a search for new compounds with central nervous system activity". Several of the intermediate compounds are the same as certain intermediates in the present application, and are prepared by the same or similar processes. The right-hand compound above is itself an intermediate in the preparation of certain of the final products claimed herein.

G. N. Walker et al., in the Journal of Organic Chemistry, 36, 305–8 (1971), disclose inter alia substituted 2,3,4,5-tetrahydro-1,4-benzoxazepines of the formulae

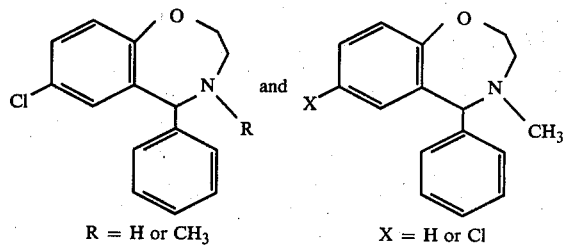

R = H or CH₃       X = H or Cl

These compounds are described as having "only moderate hypotensive (and no significant central nervous) effects". They were prepared by methods different from those utilized in the present application.

Chemical Abstracts, 73, 120697h (1970) reports that German OLS 2,014,223 describes

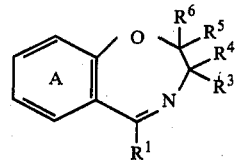

and the corresponding 2,3-dihydro compound as being tranquilizers, hypnotics and muscle relaxants. As indicated above, this compound is an intermediate in the preparation of certain of the final products claimed herein.

German OLS 2,100,654 discloses, inter alia, substituted 2,3-dihydro-1,4-benzoxazepines of the formula

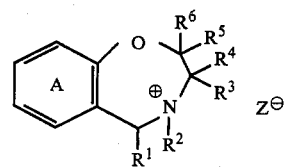

in which the fused benzene ring A may contain "one or more same or different substituents", $R^1$ may be inter alia substituted or unsubstituted phenyl and $R^3$, $R^4$, $R^5$ and $R^6$ may be hydrogen or any of a wide variety of substituted or unsubstituted alkyl, alkenyl, alkynyl, aryl, aralkyl, aryloxyalkyl, arylthioalkyl or heterocyclyl substituents. Also disclosed are acid addition salts and quaternary ammonium salts of the above compounds, having the formula

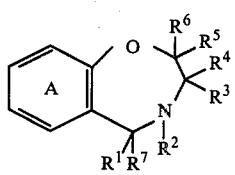

in which A, $R^1$, $R^3$, $R^4$, $R^5$ and $R^6$ are the same as above, $Z^{\ominus}$ is an anion and $R^2$ is hydrogen or an alkyl or aralkyl radical. The only $R^2$ group which is exemplified is methyl.

Belgian Patent 764,865 discloses, inter alia, substituted 2,3,4,5-tetrahydro-1,4-benzoxazepines of the formula in which the combination of $R^1$ and $R^7$ may be inter alia substituted or unsubstituted phenyl provided that at least one of $R^2$, $R^3$, $R^4$, $R^5$ or $R^6$ is other than hydrogen, and $R^2$, $R^3$, $R^4$, $R^5$, $R^6$ and A are as set forth in the preceding paragraph relating to OLS 2,100,654.

South African patent 67/05136 describes 1,3-disubstituted pyrrolidines of the formula

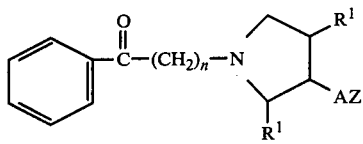

having tranquilizing and/or analgetic activity, in which inter alia AZ may be

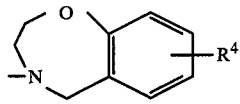

wherein R⁴ is H, (lower)alkyl, (lower)alkoxy, trifluoromethyl, halogen of molecular weight less than 80 or di(lower)alkylamino. Specifically disclosed 4-(3-pyrrolidinyl)-2,3,4,5-tetrahydro-1,4,-benzoxazepines utilized as intermediates include compounds of the formula

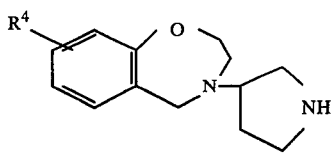

in which R⁴ is hydrogen, 9-methoxy or 8-diethylamino. No pharmaceutical activity is ascribed to these intermediates and the intermediates do not include 5-phenyl substitution or any 4-substituents other than the 4-(3-pyrrolidinyl) moiety.

In the Journal of the Chemical Society, 1137–1141 (1965), D. Huckle et al. describe inter alia compounds of the formula

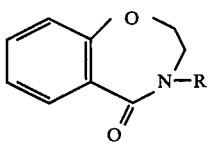

in which R may be 2-(dimethylamino)ethyl, 2-(pyrrolidino)ethyl, 2-(piperidino)ethyl, 2-(morpholino)ethyl, 3-(dimethylamino)propyl or 3-(morpholino)propyl. Where R is 2-(morpholino)ethyl, the compound may also contain a 9-methyl, 9-methoxy or 7-methoxy substituent. The compound

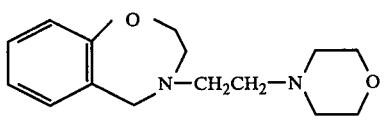

also is disclosed. No pharmaceutical activity is ascribed to any of the compounds, No 5-substituent other than oxo is disclosed.

U.S. Pat. No. 2,807,628 discloses compounds of the formula

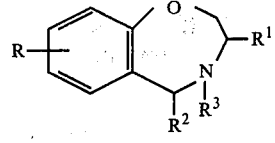

in which R is H, chloro, fluoro, (lower)alkyl, (lower)alkoxy or monocyclic alkyl, R¹ is H, alkyl or aryl, R² is H or methyl and R³ is β-chloro(lower)alkyl. The compounds are described as adrenergic blocking agents, anticholinergic agents, adrenolytic agents and/or antihistamines.

U.S. Pat. No. 3,346,565 describes substituted 1,2,3,4,5-tetrahydro-4,1-benzoxazepines of the formula

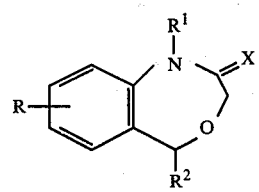

in which R is H or halogen, R¹ is alkyl, aralkyl, acyl or

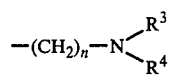

in which n is 1–5 and R³ and R⁴ are H, alkyl or, taken together with the nitrogen, may represent an optionally substituted heterocyclic ring, R² is H, alkyl, aryl or aralkyl, and X is O or H₂. Of the specifically disclosed compounds in which R¹ is

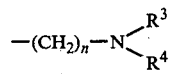

X is in each instance oxygen. It is to be noted that these compounds are 1,2,3,5-tetrahydro-4,1-benzoxazepines rather than the 2,3,4,5-tetrahydro-1,4-benzoxazepines claimed in the present application. Thus, in these prior art compounds, the ring nitrogen is immediately adjacent the fused benzene ring (rather than being further removed via an intervening carbon atom, as in the present invention) and the ring oxygen is separated from the fused benzene ring via an intervening carbon atom (rather than being immediately adjacent, as in the present invention). These differences sufficiently change the chemical character of the ring nitrogen atom, for example, so that the compounds of the present invention cannot be prepared by the process described in U.S. Pat. No. 3,346,565. Thus, that patent states that the R¹ substitutent is introduced by a "conventional" method, e.g. by reacting the compound of the formula

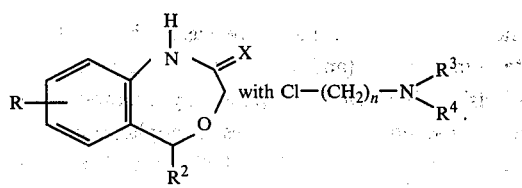

However, it has been found that the intermediates of the present invention, e.g. those of the formula

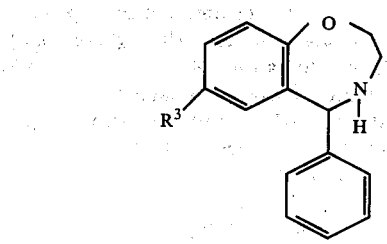

where $R^3$ is H or Cl do not react with compounds such as

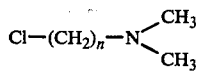

in which n is 2 or 3; only starting material was recovered.

U.S. Pat. No. 3,676,460 discloses compounds of the formula

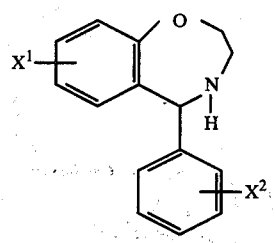

in which $X^1$ and $X^2$ are H, halogen, (lower)alkyl or (lower)alkoxy, which are stated to have strong central nervous system activity. None of these compounds have a substituent on the ring nitrogen.

U.S. Pat. No. 3,686,217 discloses compounds of the formula

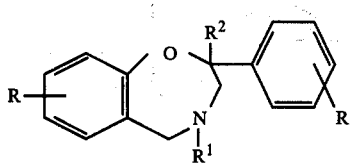

in which R is H, halogen, (lower)alkyl, (lower)alkoxy, trifluoromethyl or the like, $R^2$ is H or (lower)alkyl and $R^1$ is "a hydrocarbon radical of aliphatic character" (more particularly stated to be alkyl, alkenyl, cycloalkyl or phenylalkyl). The compounds are stated to have pronounced action on the central nervous system and to be useful as analgesics, psychotropic agents, anti-aggression agents, etc. One of the disclosed methods of preparing the above compounds is by reduction of a compound of the formula

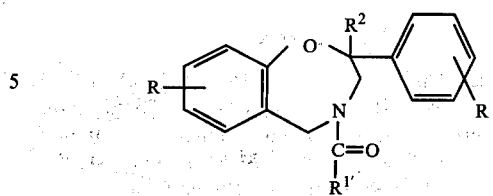

in which $R^{1'}$—$CH_2$— has the same meaning as $R^1$ with lithium aluminum hydride. However, all of these prior art compounds contain a 2-phenyl substituent not found in the instantly claimed compounds and do not contain the 5-phenyl substituent of the instantly claimed compounds. Further, the $R^1$ substituents do not resemble or suggest the ω-(dimethylamino)alkyl or ω-(pyrrolidino)alkyl substituents of the instantly claimed compounds.

U.S. Pat. No. 3,794,639 discloses, inter alia, compounds of the formula

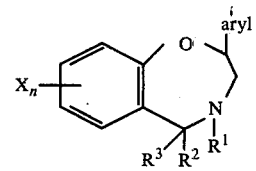

in which X may be H, halogen (lower)alkyl, (lower)alkoxy, amino, nitro, trifluoromethyl, etc., $R^2$ and $R^3$ are H or, taken together, may be O, and $R^1$ may be inter alia —AB in which A is a (lower)alkylene group and B is a basic N-containing radical of less than 12 carbon atoms. The $R^1$ group is introduced by reacting the desired 1,4-benzoxazepin-5-one with either (1) BA-halogen or (2) halogen-A-halogen and subsequent reaction of the intermediate product with H-B. To obtain compounds in which $R^2$ and $R^3$ are H, the 5-oxo group is subsequently reduced with $LiAlH_4$. Of the 21 examples in the patent, 20 describe the preparation of benzothiazepines and only one deals with a benzoxazepine; it discloses 7-methoxy-3,4-dihydro-2-furyl-2H-1,4-benzoxazepin-5-one. It is to be noted that all compounds disclosed therein contain a 2-aryl substituent (not present in the instantly claimed compounds) and do not contain a 5-phenyl substituent as in the instantly claimed compounds. The compounds are stated to have CNS modifying activity and to be useful as tranquilizers.

Derwent Abstract 39846F indicates that Dutch Patent No. 69.04326 discloses 3-aryl-4-(disubstituted aminoalkyl)-1,4-benzoxazepin-5-(4H)-ones having anti-inflammatory and analgesic activity. Specifically disclosed is the compound of the formula

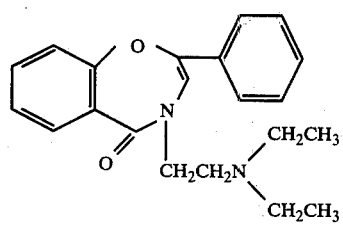

These compounds are not tetrahydro, cannot contain a 5-phenyl substituent, and do contain 3-phenyl and 5-oxo substituents not contained in the instantly claimed compounds.

SUMMARY

The present invention relates to novel substituted 2,3,4,5-tetrahydro-1,4-benzoxazepines, and acid addition salts thereof, having pharmacological activity, and to a process for their preparation. More particularly, this invention relates to compouns of the formula

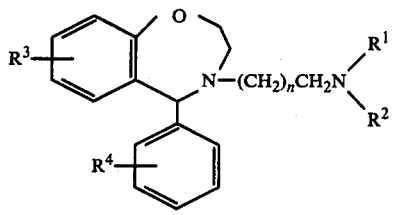

wherein $R^1$ and $R^2$ each represent methyl or, when taken together with the nitrogen to which they are attached, represent pyrrolidino, $R^3$ and $R^4$ are the same or different and represent hydrogen, chloro, fluoro, bromo, iodo, nitro, (lower)alkyl, trifluoromethyl, (lower)alkoxy, trifluoromethoxy or (lower)alkylthio, and n is an integer from 1 to 4, and nontoxic, pharmaceutically acceptable acid addition salts thereof, and to the process for their preparation. These compounds are valuable analgesic and/or antitussive agents.

The compounds disclosed herein are numbered according to the numbering of the basic 1,4-benzoxazepine ring system, as follows:

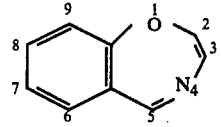

The compounds of the present invention may be prepared by the following illustrative sequence of steps.

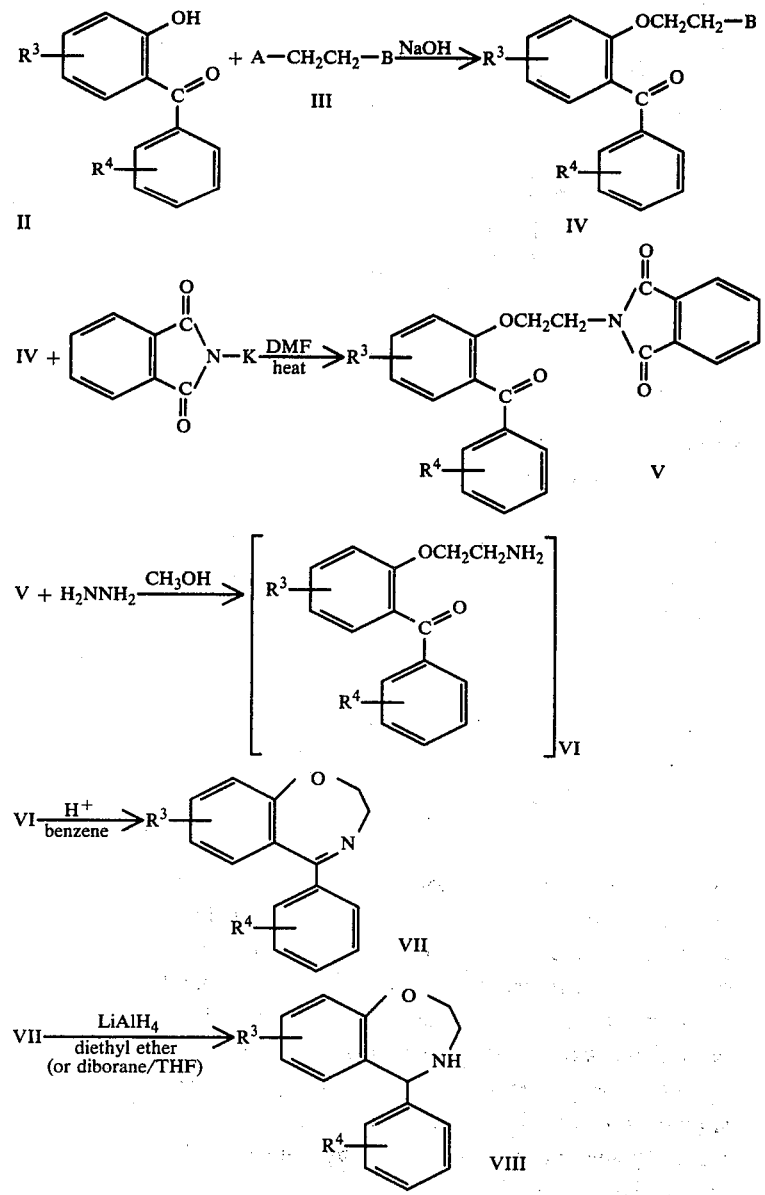

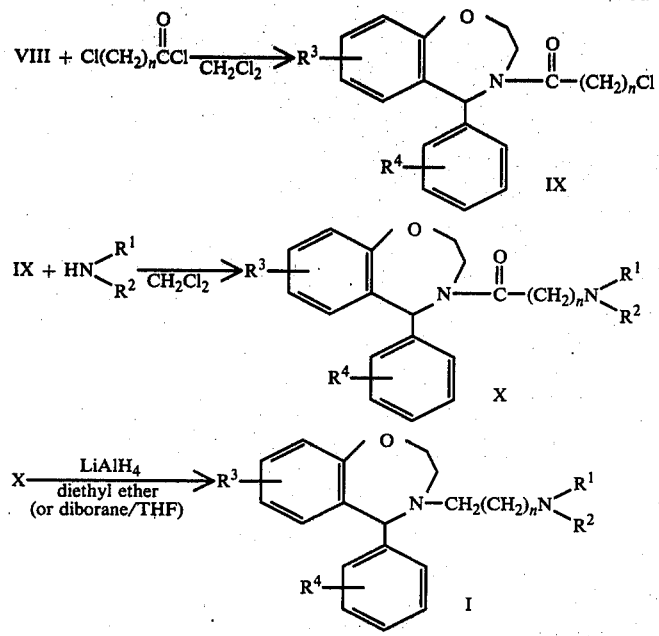

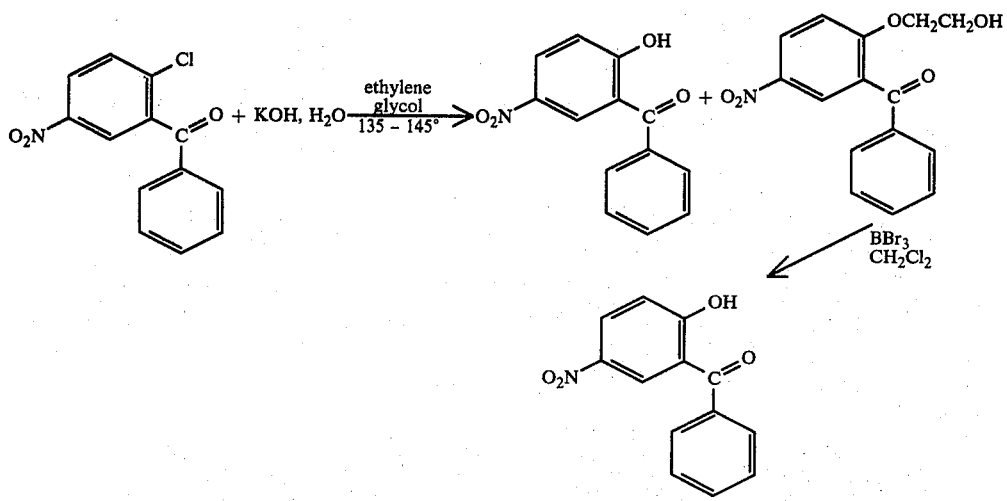

A and B in compound III above reprerent two displaceable groups of different reactivities, e.g. chloro and p-toluenesulfonyl, or chloro and bromo. If A and B are the same, the chief product is a dimer. I prefer to utilize 2-chloroethyl-p-toluenesulfonate as compound III.

Compound VIII was conveniently prepared in a single process from compound V, without purification of compounds VI or VII. Similarly, the products of formula I were prepared in a single process from compound VIII, without purification of compounds IX or X.

The substituted 2-hydroxybenzophenones of formula II used as starting materials in the above procedure may be prepared by procedures well known in the art, e.g. as described in U.S. Pat. No. 2,419,553 and, where $R^3$ and $R^4$ are nitro, by the procedure described in Chemische Berichte, 31, 1696 (1898). A particularly elegant improvement on the Berichte process, which gives 2-hydroxy-5-nitrobenzophenone in greater than 80% overall yield, is as follows:

DESCRIPTION OF THE PREFERRED EMBODIMENTS

Preferred compounds of formula I, above, are those having the formula

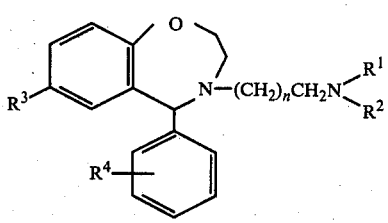

in which $R^1$ and $R^2$ each are methyl or, when taken together with the nitrogen to which they are attached, represent pyrrolidino, $R^3$ and $R^4$ are the same or different and represent hydrogen, chloro, fluoro, bromo, iodo, nitro or trifluoromethyl, and n is an integer from 1 to 4, and nontoxic pharmaceutically acceptable acid addition salts thereof.

More preferred compounds are those of formula Ia in which R¹ and R² each are methyl or, when taken together with the nitrogen to which they are attached, represent pyrrolidino, R³ is hydrogen, chloro, fluoro, bromo, iodo, nitro or trifluoromethyl, R⁴ is hydrogen, 4-chloro or 2-fluoro (and preferably hydrogen), and n is an integer from 1 to 4, and nontoxic pharmaceutically acceptable acid addition salts thereof.

Even more preferred compounds are those of formula Ia in which R¹ and R² each are methyl or, when taken together with the nitrogen to which they are attached, represent pyrrolidino, R³ is chloro, R⁴ is hydrogen and n is an integer of 1 to 4 (and preferably n is 1), and nontoxic pharmaceutically acceptable acid addition salts thereof.

A most preferred compound is 7-chloro-4-(2-dimethylaminoethyl)-5-phenyl-2,3,4,5-tetrahydro-1,4-benzoxazepine, and nontoxic pharmaceutically acceptable acid addition salts thereof (and preferably the dihydrochloride salt).

Another most preferred compound is 7-chloro-4(2-pyrrolidinoethyl)-5-phenyl-2,3,4,5-tetrahydro-1,4-benzoxazepine, and nontoxic, pharmaceutically acceptable acid addition salts thereof (and preferably the dihydrochloride).

This invention also relates to a process for the preparation of the compounds of formula I. Accordingly, another preferred embodiment of the present invention is a process for the preparation of a compound having the formula

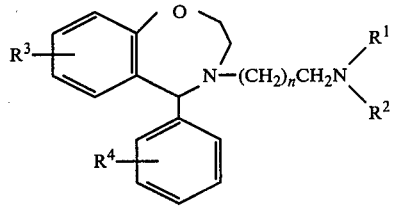

I wherein R¹ and R² each represent methyl or, when taken together with the nitrogen to which they are attached, represent pyrrolidino, R³ and R⁴ are the same or different and represent hydrogen, chloro, fluoro, bromo, iodo, nitro, (lower)alkyl, trifluoromethyl, (lower)-alkoxy, trifluoromethoxy or (lower)alkylthio, and n is an integer from 1 to 4, and nontoxic, pharmaceutically acceptable acid addition salts thereof, which process comprises reacting a compound having the formula

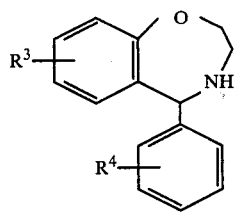

VIII in which R³ and R⁴ are as defined above, with an acylating derivative of an acid of the formula

X—(CH₂)ₙ—COOH in which X is chloro, bromo, fluoro, iodo, p-toluenesulfonyl or trifluoromethanesulfonyl, and n is as defined above, in a nonreactive organic solvent, at a temperature of from about 0° C to about 100° C, to produce a compound having the formula

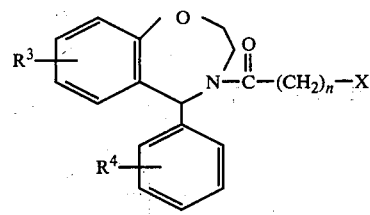

IX in which R³, R⁴, n and X are as defined above, and reacting compound IX with an amine of the formula

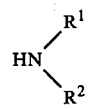

in which R¹ and R² are as defined above, in a non-reactive organic solvent, at a temperature of from about 0° C to about 100° C, to produce a compound having the formula

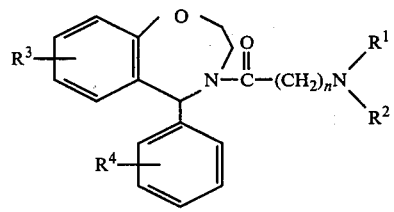

X in which R¹, R², R³, R⁴ and n are as defined above, and reducing compound X with lithium aluminum hydride or diborane, in a solvent selected from an ether, tetrahydrofuran and ether-hydrocarbon mixtures, at a temperature of from about 0° C to about 100° C, provided that, when R³ or R⁴ is nitro, the reducing agent is diborane in tetrahydrofuran, and, if desired, converting the product to a nontoxic, pharmaceutically acceptable acid addition salt.

In a more preferred embodiment of the above process, R³ is in the 7-position and R³ and R⁴ are the same or different and each represent hydrogen, chloro, fluoro, bromo, iodo, nitro or trifluoromethyl.

In an even more preferred embodiment of the above process, R³ is in the 7-position and represents hydrogen, chloro, fluoro, bromo, iodo, nitro, or trifluoromethyl, and R⁴ is hydrogen, 4-chloro or 2-fluoro (but preferably hydrogen).

The acids which may be used to form nontoxic, pharmaceutically acceptable salts with the compounds of the present invention are well known to those skilled in the art. They include inorganic and organic acids such as, hydrochloric, hydrobromic, sulfuric, nitric, phosphoric, formic, acetic, propionic, succinic, glycolic, lactic, malic, tartaric, citric, ascorbic, maleic, pyruvic, phenylacetic, benzoic, p-aminobenzoic, salicylic, methanesulfonic, ethanesulfonic, toluenesulfonic, and the like. The preferred acid is hydrochloric.

Referring to the general reaction scheme set forth above, the reaction of compound VIII with the acylating agent to produce compound IX may be conducted in any non-reactive organic solvent, e.g. methylene chloride, chloroform, carbon tetrachloride, benzene, toluene, xylene, diethyl ether, tetrahydrofuran, dioxane, diglyme or monoglyme. I prefer to use methylene chloride. The reaction temperature is not critical, the reaction may be conducted over a temperature range of from about 0° C to 100° C (or to the reflux temperature of the solvent, in the case of lower-boiling solvents). It is most convenient to conduct the reaction at room temperature. The acylating acid $X-(CH_2)_n-COOH$ may be in the form of any of the acylating derivatives which are known for use in acylating a secondary amine, e.g. its acid halide, activated ester, carbodiimide, or the like. The acid chloride is preferred. Substituent X is chloro, bromo, fluoro, iodo, p-toluenesulfonate or trifluoromethanesulfonate. It is preferred that X be chloro.

In the reaction of compound IX with an amine to produce compound X, one may use the same non-reactive organic solvents and the same temperature range as set forth above for the preparation of compound IX. It is preferred to conduct the reaction in methylene chloride. When using a low-boiling amine such as the normally gaseous dimethylamine, it is preferred to conduct the reaction at low temperature, e.g. 0° C; alternatively, the reaction may be conducted at room temperature in a sealed vessel. Room temperature is preferred for higher boiling amines.

The reduction of compound X to produce compound I (when neither $R^3$ nor $R^4$ is nitro) may be accomplished by the use of lithium aluminum hydride or diborane in an ether, tetrahydrofuran or an ether-hydrocarbon mixture. When $R^3$ and/or $R^4$ are nitro, the reduction is accomplished with diborane in tetrahydrofuran. The reaction temperature is not critical and may range from about 0° C to about 100° C (or up to the reflux temperature of the solvent, in the case of lower-boiling solvents).

It is to be noted that the compounds of formula I contain an asymmetric carbon atom and therefore may exist as optical isomers. Both the optical isomers and the racemic mixtures of the compounds of formula I are included within the scope of this invention.

It has surprisingly been found that the compounds of this invention have valuable analgesic and/or antitussive activity, while other very closely related compounds have little or no such activity. Thus, a preferred compound of this invention, 7-chloro-4-(2-dimethylaminoethyl)-5-phenyl-2,3,4,5-tetrahydro-1,4-benzoxazepine is an effective analgesic and antitussive agent, while the very closely related compounds, 7-chloro-4-(2-methylaminoethyl)-5-phenyl-2,3,4,5-tetrahydro-1,4-benzoxazepine and 7-chloro-4-(2-diethylamino)-5-phenyl-2,3,4,5-tetrahydro-1,4-benzoxazepine have little or no such activity.

Similarly, another preferred compound of this invention, 7-chloro-4-(2-pyrrolidinoethyl)-5-phenyl-2,3,4,5-tetrahydro-1,4-benzoxazepine, has valuable analgesic activity, while the very closely related compounds containing morpholino, piperidino or 4-methylpiperazino in place of pyrrolidino, have little or no analgesic activity.

Compounds of formula I, and homologous and analogous compounds, were tested for analgesic activity by means of the phenylquinone-induced writhing test in the mouse, using the known analgesic, nefopam (5-methyl-1-phenyl-3,4,5,6-tetrahydro-1H-2,5-benzoxazocine), as a comparison standard. The method used was essentially that described by Siegmund et al. [Proc. Soc. exp. Biol. N. Y. 95, 729 (1957)]. Compounds were administered either subcutaneously (15 min) or orally (25 min) prior to the intraperitoneal injection of phenylquinone (2 mg/kg). Beginning 5 min after the phenylquinone injection, the animals were observed for writhing and the number of writhes over a 10 min period was determined. The dose which produced a 50 percent reduction in the number of writhes, as compared to the control group, was called the $ED_{50}$. The results of the tests are shown in Table 1.

TABLE 1

Phenylquinone-induced Writhing Test In The Mouse

| $-N\begin{matrix}R^1\\R^2\end{matrix}$ | | Compound No. | $ED_{50}$ (mg./kg., s.c.) |
|---|---|---|---|
| — | (nefopam) | — | 1.1 |
| dimethylamino | | BL-R845 | 1.3 |
| diethylamino | | BL-5372 | 10. |
| methylamino | | BL-5366 | 13. |
| pyrrolidino | | BL-5397 | 2.5 |
| morpholino | | BL-5405 | >40. |
| piperidino | | BL-5409 | 9. |
| 4-methylpiperazino | | BL-5451 | 19. |

Compounds of formula I, and homologous and analogous compounds, were also tested for antitussive activity in male guinea-pigs, using a modification of the procedure of Friebel and Hahn [Med. Pharmacol. exp., 14, 78 (1966)]. Under general anesthesia, two stainless steel wires (0.2 mm diameter), stripped of their enamel insulation at the points of contact with the trachea, were wrapped around the trachea about 8 mm apart and then threaded under the skin and out through the back of the neck, one on each side. After 24 hrs, test animals were placed in a clear plastic cage and the cough threshold was determined by means of electrical stimulation. The following stimulation parameters were used: delay — 0.01 msec, duration — 0.6 msec and frequency — 300 Hz. The minimal voltage (range 60–120 V) necessary to elicit a cough in less than 6 sec was determined. Each guinea-pig was stimulated 5 times at 30 sec intervals employing the predrug stimulation parameters at 30, 60 and 120 min following drug administration. A test animal was considered to be protected if more than 6 sec were required to produce a cough. Compounds were administered at a dosage of 10 mg./kg. subcutaneously. The percent inhibition of cough response was calculated as follows:

% Inhibition = $(A-B)/(A) \times 100$

A = number of coughs requiring <6 sec. stimulation after saline.

B = number of coughs requiring <6 sec. stimulation after drug.

The results of the test are shown in Table 2.

Table 2
Antitussive Activity in Male Guinea-pigs $-N\diagdown \substack{R^1 \\ R^2}$

| | Compound No. | % Inhibition of Cough |
|---|---|---|
| — (nefopam) | — | 0 |
| dimethylamino | BL-R845 | 48 |
| diethylamino | BL-5372 | 0 |
| methylamino | BL-5366 | 0 |
| pyrrolidino | BL-5397 | 0 |
| morpholino | BL-5405 | 30 * |
| piperidino | BL-5409 | 0 |
| 4-methylpiperazino | BL-5451 | 0 |

* Values of 30 or less are not significantly different from saline controls, and such compounds are considered inactive or insufficiently active to be of interest.

The antitussive activity of BL-R845 and nefopam were determined in dogs by the method of Stefko and Benson [j. Pharmacol. exp. Ther., 108, 217 (1953)] and the results are shown in Table 3. Compound BL-R845 is seen to be more active than nefopam or codeine, by both routes of administration.

Table 3
Antitussive Activity In The Dog

| | $ED_{50}$ (mg. kg.) | |
|---|---|---|
| Compound | s. c. | oral |
| BL-R845 | 0.2–0.5 | 2–5 |
| nefopam | 2–5 | >20 |
| codeine | 1.5 | 7.8 |

BL-R845 and nefopam were compared in additional phenylquinone-induced writhing tests in the mouse and rat, by various routes of administration. The results are shown in Table 4.

Table 4
Phenylquinone-induced Writhing — $ED_{50}$ (mg./kg.)

| | Mice | | | Rats | |
|---|---|---|---|---|---|
| Compound | sub-cutaneous | intra-ventricular | oral | sub-cutaneous | oral |
| BL-R845 | 1.3 | 0.31 | 11.6 | 1.0 | 12.8 |
| nefopam | 1.1 | 0.14 | 22 | 1.0 | 9.6 |

The analgesic profile for BL-R845 and nefopam resembles that of the narcotic antagonist analgesics rather than the narcotic drugs. This observation is based on their relative lack of analgesic activity in the conventional thermal analgesic tests, i.e. mouse hot plate and rat tail flick, and their good activity in the rodent writhing tests. Nevertheless, both BL-R845 and nefopam differ from the antagonist action of naloxone. Naloxone does not block the analgesic activity of either BL-R845 or nefopam. These findings indicate that BL-R845 and nefopam act on different receptor sites from those affected by the antagonist analgesics.

The compounds of this invention are useful analgesic and/or antitussive agents in mammals, including man. The dosage of the compounds of this invention will depend on the particular compound employed, the route of administration and the degree of effect desired. However, in general, satisfactory results are obtained when administered 3–4 times a day at doses of from about 0.1 to 10.0 mg./kg. of body weight. The compounds may be administered in any of the conventional forms, e.g. orally as capsules, tablets, suspensions or solutions, parenterally as sterile solutions or suspensions. The compounds may be administered alone or in pharmaceutical compositions containing suitable pharmaceutical carriers, diluents, preserving agents, suspending agents, binding agents, lubricating agents, and the like. Such compositions are prepared by methods known in the art. The free basic amino compounds, while effective, are preferably formulated and administered in the form of their nontoxic, pharmaceutically acceptable acid addition salts.

As used herein the terms (lower)alkyl, (lower)alkoxy and (lower)alkylthio mean an alkyl, alkoxy or alkylthio group containing from 1 to 6 carbon atoms.

EXAMPLE 1

5-Chloro-2-(2-chloroethoxy)benzophenone

To a stirred solution of 150.0 g (0.639 mole) of 2-chloroethyl-p-toluenesulfonate and 129.3 g (0.55 mole) of 5-chloro-2-hydroxybenzophenone in 1000 ml of toluene was added all at once 25.6 g (0.639 mole) of NaOH flakes. The mixture was heated to reflux under a Dean-Stark water separator. The thick yellow solid which initially formed gradually disapperared and a second solid separated soon after the mixture reached reflux.

After 17 hours the reaction mixture was cooled and water was added to dissolve the precipitated sodium tosylate. The organic layer was separated and washed with two portions each of water, 10% NaOH solution, water, 2N HCl, saturated $NaHCO_3$ solution and water. The organic solution was dried (anhydrous $MgSO_4$) and evaporated under reduced pressure. The yellowish residue was recrystallized from 150 ml of methanol to give 114.1 g (60% yield) of colorless solid, mp 75°–77° (literature gives mp 73°–74.5°).

EXAMPLE 2

5-Chloro-2-(2-N-phthalimidoethoxy)benzophenone

Potassium phthalimide (60.2 g, 0.325 mole), 80.0 g (0.271 mole) of 5-chloro-2-(2-chloroethoxy)benzophenone and 1000 ml of dimethylformamide were stirred and refluxed, under anhydrous conditions, for 16 hours. The dark mixture was cooled, diluted with 650 ml of $CHCl_3$ and poured into 2000 ml of water. The organic layer was separated and the aqueous alkaline layer was extracted with three portions of $CHCl_3$. The combined organic solutions were washed with 200 ml of 5% NaOH solution and with three portions of water, and were dried over anhydrous $Na_2SO_4$.

The solvent was removed under reduced pressure and the amber syrup thus obtained was dissolved in hot methanol, cooled, and scratched to induce crystallization. The straw-colored solid was filtered off, washed with cold methanol, and dried to give 82.8 g (75% yield) of product, mp 119°–120° (literature gives mp 114°–115°).

EXAMPLE 3

7-Chloro-5-phenyl-2,3,4,5-tetrahydro-1,4-benzoxazepine hydrochloride a. 2-(2-Aminoethoxy)-5-chlorobenzophenone To a hot solution of 87.7 g (a0.216 mole) of 5-chloro-2-(2-N-phthalimidoethoxy)benzophenone in 1500 ml of methanol was added all at once 7.25 ml (7.33 g, 0.227 mole) of anhydrous hydrazine. The solution was relfuxed for 16 hours and then evaporated under reduced pressure.

The solid residue was digested on the steam bath for one hour with 500 ml of 6N HCl; the mixture was then refluxed for one hour, cooled, and chilled at 5° overnight. The crystalline phthalhydrazide was filtered off. The filtrate was cooled in ice and made strongly alkaline with 40% NaOH solution. The amine which separated was extracted out with three portions of diethyl ether. The combined extracts were washed with saturated brine and dried over anhydrous $Na_2SO_4$. The solvent was evaporated under reduced pressure to give 59.6 g (64% yield) of crude product as a yellowish oil. This was used without purification in the next step.

b. 7-Chloro-2,3-dihydro-5-phenyl-1,4-benzoxazepine and hydrochloride

A solution of 148.1 g (0.537 mole) of crude 2-(2-aminoethoxy)-5-chlorobenzophenone produced in step (a) and 20 ml of glacial acetic acid in 2000 ml of benzene was refluxed under a Dean-Stark water separator. After 16 hours separation of water was complete. The yellow solution was cooled, washed with 10% NaOH solution (two portions) and water (three portions) and dried over anhydrous $Na_2SO_4$. The solvent was removed under reduced pressure to give 144.0 g (quantitative yield) of product as a thick yellow oil which crystallized upon standing at 0°. This material was used without purification in the following step.

A small portion of the product was converter to the HCl salt under anhydrous conditions; mp 214.5–215.5° (dec) after recrystallization from acetone.

Anal. Calculated for $C_{15}H_{12}ClNO \cdot HCl$: C, 61.24; H, 4:45; N, 4.76; Found: C, 61.35; H, 4.54; N, 4.72.

c. 7-Chloro-5-phenyl-2,3,4,5-tetrahydro-1,4-benzoxazepine hydrochloride

To a stirred suspension of 64.3 g (1.69 moles) of $LiAlH_4$ in 1500 ml of anhydrous diethyl ether was added a solution of 144.0 g (0.537 mole) of crude 7-chloro-2,3-dihydro-5-phenyl-1,4-benzoxazepine produced in step (b) in 1000 ml of anhydrous diethyl ether, at a rate sufficient to maintain reflux. The mixture was initially blue, changing to a dark green which lightened with time. After addition was complete the mixture was stirred and refluxed for two hours. The reaction mixture was cooled and cautiously decomposed by the dropwise addition of 64.2 ml of water, followed by 64.2 ml of 15% NaOH solution and finally 192.6 ml of water. Stirring was continued for 30 minutes and then the inorganic solid was filtered off. The filter cake was washed well with diethyl ether and the combined filtrate and washings were dried over anhydrous $Na_2SO_4$.

The ethereal solution of the amine was concentrated to ½ volume and the salt was formed with HCl gas. The solid was filtered off, washed with diethyl ether and recrystallized from ca. 2200 ml of methanol. There was obtained 91.0 (57%) of product as a colorless solid, mp 302°–305° (dec) (literature gives mp 278°–280° (dec)).

The overall yield of steps (b) and (C) was 36%.

EXAMPLE 4

7-Chloro-4-(2-dimethylaminoethyl)-5-phenyl-2,3,4,5-tetrahydro-1,4-benzoxazepine dihydrochloride a. 7-Chloro-4-(2-chloroacetyl)-5-phenyl-2.3.4.5-tetrahydro-1,4-benzoxazepine 7-Chloro-5-phenyl-2,3,4,5-tetrahydro-1,4,-benzoxazepine hydrochloride (4.6 g 15.5 millimoles) was dissolved in 150 ml of hot aqueous methanol. The solution was made basic with 40% NaOH solution and concentrated on the steam bath. The remaining methanol was evaporated under reduced pressure and the mixture was extracted with diethyl ether (three portions) and then with $CH_2Cl_2$ (two portions). The combined extracts were dried (anhydrous $Na_2SO_4$) and evaporated to give 3.9 g of colorless, oily amine.

A solution of the free base and 1.71 g (17 millimoles) of triethylamine in 40 ml of $CH_2Cl_2$ was added dropwise, under argon, to a stirred solution of 1.93 g (17 millimoles) of chloroacetyl chloride in 35 ml of $CH_2Cl_2$. The solution was stirred at ambient temperature for four hours and then stored, under argon, for 16 hours at 0°.

The solution was washed with 10% HCl solution (three portions), water (two portions), 10% $NaHCO_3$ solution (two portions) and saturated brine (one portion) and dried (anhydrous $Na_2SO_4$). Evaporation of the solvent and stripping the residue in vacuo gave 4.78 g (95%) of product as a foam. This was used directly in the next step.

b. 7-Chloro-4-(2-dimethylaminoacetyl)-5-phenyl-2,3,4,5-tetrahydro-1,4-benzoxazepine A solution of 4.78 g (14.2 millimoles) of the 7-chloro-4-(2-chloroacetyl)-5-phenyl-2,3,4,5-tetrahydro-1,4-benzoxazepine produced in step (a) in 150 ml of $CH_2Cl_2$ was saturated with dimethylamine gas at 0°. The flask was stoppered and the solution was stored at $-15°$ for 16 hours.

Dimethylamine gas was again bubbled through the solution for ca. 30 minutes at 0°. The solution was warmed at 50° for ca. 15 minutes and then degassed with $N_2$. The organic solution (containing some solid) was then washed with three portions of saturated $NaHCO_3$ solution and dried over anhydrous $Na_2SO_4$. Removal of the solvent gave 4.87 g (quantitative yield) of product as a yellow, viscous oil. The product failed to crystallize and was used directly in the final step.

c. 7-Chloro-4-(2-dimethylaminoethyl)-5-phenyl-2,3,4,5-tetrahydro-1,4-benzoxazepine dihydrochloride A stirred solution, under $N_2$, of 7-chloro-4-(2-dimethylaminoacetyl)-5-phenyl-2,3,4,5-tetrahydro-1,4-benzoxazepine produced in step (b) (4.8 g, 14.2 millimoles) in 150 ml of tetrahydrofuran was treated dropwise, at room temperature with 85 ml (84 millimoles) of diborane in tetrahydrofuran (0.98M in $BH_3$). After addition the solution was stirred for 45 minutes and then refluxed for 20 hours.

The reaction mixture was cautiously decomposed by the dropwise addition of 100 ml of 10% HCl solution. The tetrahydrofuran was removed under reduced pressure and the aqueous solution remaining was made basic with 40% NaOH solution. The product was extracted out with diethyl ether (5 portions). The combined extracts were washed (saturated brine), dried (anhydrous $Na_2SO_4$) and evaporated to give an oil. This material was still a boron complex and was decomposed by heating on the steam bath for 16 hours with an excess of 10% HCl. The solution thus obtained was worked up as before and the salt of the oily amine was formed with HCl gas in anhydrous diethyl ether. The ethereal mixture was evaporated and the foamy solid was crystallized from absolute ethanol-diethyl ether. The crude salt was recrystallized from absolute ethanol to give 1.85 g (34%) of the title compound as colorless crystals, mp 235°–236°.

Anal. Calculated for $C_{19}H_{23}ClN_2O \cdot 2HCl$: C, 56.51; H, 6.24; N, 6.94; Found: C, 56.54; H, 6.35; N, 6.81.

EXAMPLE 5

7-Chloro-4-(2-methylaminoethyl)-5-phenyl-2,3,4,5-tetrahydro-1,4,-benzoxazepine dihydrochloride a. Crude 7-chloro-4-(2-chloroacetyl)-5-phenyl-2,3,4,5-tetrahydro-1,4-benzoxazepine, prepared as described in Example 4a starting with 7-chloro-5-phenyl-2,3,4,5-tetrahydro-1,4-benzoxazepine (1.82 g, 7.0 millimoles), was dissolved in 125 ml $CH_2Cl_2$ and the solution was saturated with gaseous monomethylamine. The reaction solution was stoppered and allowed to stand at room temperature for 18 hours, followed by unstoppering and warming on a steam bath for 30 minutes. The resulting $CH_2Cl_2$ solution was washed with two portions of saturated $NaHCO_3$, dried over $Na_2SO_4$, filtered and rendered free of solvent to afford crude 7-chloro-4-(2-methylaminoacetyl)-5-phenyl-2,3,4,5-tetrahydro-1,4-benzoxazepine as a light viscous oil which was used directly in the next step without further purification.

b. The crude amide from step (a) was dissolved in 20 ml dry diethyl ether and added slowly, with vigorous stirring, to a suspension of $LiAlH_4$ (0.46 g, 12.1 millimoles) in 30 ml dry diethyl ether. After allowing the reaction mixture to reflux for 18 hours and cooling, there was added slowly with vigorous stirring, 0.9 ml $H_2O$ and 0.7 ml 10% NaOH. The resulting mixture was stirred at room temperature for 1.5 hours. After filtration and evaporation of the filtrate, the crude title compound was obtained as a light colored oil. A dihydrochloride salt was prepared and recrystallized from methanol-diethyl ether; mp 221°–223°(1.12 g; 41%).

Anal. Calculated for $C_{18}H_{21}ClN_2O \cdot 2HCl$: C, 55.47; H, 5.95; N, 7.19; Cl, 27.29. Found: C, 54.00; H, 6.14; N, 7.05; Cl, 26.02; $H_2O$, 1.58. Corrected for $H_2O$: C, 55.68; H, 6.06; N, 7.16; Cl, 26.44.

EXAMPLE 6

7-Chloro-4-(2-diethylaminoethyl)-5-phenyl-2,3,4,5-tetrahydro-1,4-benzoxazepine dihydrochloride 7-Chloro-4-(2-chloroacetyl)-5-phenyl-2,3,4,5-tetrahydro-1,4-benzoxazepine (2.3 g, 8.8 millimoles), prepared as described in Example 4a was dissolved in 100 ml $CH_2Cl_2$, to which solution was added diethylamine (6.5 g; 88.0 millimoles). The resulting solution was allowed to stir at room temperature for 18 hours after which the solvent was removed. The residue was extracted with diethyl ether. The ethereal solution was washed with three portions of $H_2O$, with brine, and was dried over $Na_2SO_4$, filtered and evaporated, thereby affording crude 7-chloro-4-(2-diethylaminoacetyl)-5-phenyl-2,3,4,5-tetrahydro-1,4-benzoxazepine as a viscous oil. The crude material was reduced with $LiAlH_4$ (0.55 g; 14.6 millimoles) in diethyl ether by the general procedure of Example 5. The dihydrochloride salt was prepared, thereby affording a 52% yield of the title compound; mp 113° C (dec).

Anal. Calculated for $C_{21}H_{27}ClN_2O \cdot 2HCl$: C, 58.40; H, 6.77; N, 6.49; Cl, 24.63. Found: C, 57.29; H, 7.01; N, 6.38; Cl, 23.16; $H_2O$, 2.19. Corrected for $H_2O$: C, 58.57; H, 6.92; N, 6.52; Cl, 23.67.

EXAMPLE 7

7-Chloro-4-(1-oxo-2-pyrrolidinoethyl)-5-phenyl-2,3,4,5-tetrahydro-1,4-benzoxazepine hydrochloride To a solution of 7-chloro-4-(2-chloroacetyl)-5-phenyl-2,3,4,5-tetrahydro-1,4-benzoxazepine (3.5 g, 10.4 millimoles) prepared as described in Example 4a, in 100 ml $CH_2Cl_2$, was added pyrrolidine (7.2 g, 104 millimoles). The resulting reaction solution was allowed to stir at room temperature for 18 hours, after which it was evaporated to dryness. The residue was dissolved in ether and the resulting ethereal solution was washed with two portions of $H_2O$, with brine, and was dried over $Na_2SO_4$, filtered and evaporated to dryness. The residue so obtained was dissolved in $CH_3CH$-diethyl ether and a hydrochloride salt was prepared. There was obtained a 81.8% yield of the title compound; mp 280°–282°.

Anal. Calculated for $C_{21}H_{23}ClN_2O_3 \cdot HCl$: C, 61.92; H, 5.94; N, 6.88; Cl, 17.41.

Found: C, 61.44; H, 5.88; N, 7.02; Cl, 17.24; $H_2O$, 0.9. Corrected for $H_2O$: C, 62.00; H, 5.83; N, 7.08; Cl, 17.40.

EXAMPLE 8

7-Chloro-4-(1-oxo-2-morpholinoethyl)-5-phenyl-2,3,4,5-tetrahydro-1,4-benzoxazepine hydrochloride The procedure as described in Example 7 was repeated except that morpholine was used in place of pyrrolidine. The hydrochloride salt was prepared from methanol-diethyl ether in 59.6% yield; mp 248°–249° C.

Anal. Calculated for $C_{21}H_{23}ClN_2O_3 \cdot HCl$: C, 59.58; H, 5.71; N, 6.62. Found: C, 59.52; H, 5.65; N, 6.71.

EXAMPLE 9

7-Chloro-4-(1-oxo-2-piperidinoethyl)-5-phenyl-2,3,4,5-tetrahydro-1,4-benzoxazepine hydrochloride The procedure as described in Example 7 was repeated except that piperidine was used in place of pyrrolidine. The hydrochloride salt was prepared from methanol-diethyl ether in 81% yield; mp 267°–269° C.

Anal. Calculated for $C_{22}H_{25}ClN_2O_2 \cdot HCl$: C, 62.71; H, 6.22; N, 6.65; Cl, 16.83. Found: C, 61.84; H, 6.19; N, 6.53; Cl, 16.41; $H_2O$, 0.5.

Corrected for $H_2O$: C, 62.15; H, 6.17; N, 6.56; Cl, 16.49.

EXAMPLE 10

7-Chloro-4-[1-oxo-2-(4-methyl-1-piperazino)ethyl]-5-phenyl-2,3,4,5-tetrahydro-1,4-benzoxazepine The procedure as described in Example 7 was repeated except that 1-methylpiperazine was used in place of pyrrolidine. The dihydrochloride salt was prepared from ethanol-diethyl ether in 78.9% yield; mp 254°–256° C.

Anal. Calculated for $C_{22}H_{26}ClN_3O_2 \cdot HCl$:

C, 55.88; H, 5.97; N, 8.89; Cl, 22.50.

Found: C, 54.55; H, 6.04; N, 8.79; Cl, 21.75; $H_2O$, 2.67.

Corrected for $H_2O$: C, 56.05; H, 5.90; N, 9.03; Cl, 22.34.

EXAMPLE 11

7-Chloro-4-(2-pyrrolidinoethyl)-5-phenyl-2,3,4,5-tetrahydro-1,4-benzoxazepine dihydrochloride The product of Example 7 (in free base form) was reduced with $LiAlH_4$ diethyl ether by the general procedure of Example 5. The dihydrochloride salt was prepared and recrystallized from methanol-diethyl ether; 70.7% yield; mp 229°–231° C.

Anal. Calculated for $C_{21}H_{25}ClN_2O \cdot 2HCl$: C, 58.68; H, 6.33; N, 6.52.

Found: C, 58.60; H, 6.27; N, 6.71.

EXAMPLE 12

7-Chloro-4-(2-morpholinoethyl)-5-phenyl-2,3,4,5-tetrahydro-1,4-benzoxazepine dihydrochloride The product of Example 8 (in free base form) was reduced with $LiAlH_4$ in diethyl ether by the general procedure of Example 5. The dihydrochloride salt was prepared and recrystallized from ethanol-diethyl ether; 81.6% yield; mp 153° C (dec).

Anal. Calculated for $C_{21}H_{25}ClN_2O_2 \cdot HCl$:
C, 56.57; H, 6.11; N, 6.29.

Found C, 54.57; H, 6.58; N, 5.78; $H_2O$, 3.33.

Corrected for $H_2O$: C, 56.45; H, 6.43; N, 5.98.

EXAMPLE 13

7-Chloro-4-(2-piperidinoethyl)-5-phenyl-2,3,4,5-tetrahydro-1,4-benzoxazepine dihydrochloride The product of Example 9 (in free base form) was reduced with $LiAlH_4$ in diethyl ether by the general procedure of Example 5. The dihydrochloride salt was prepared and twice recrystallized from methanol-diethyl ether; 74.8% yield; mp 234°–236° C.

Anal. Calculated for $C_{22}H_{27}ClN_2O \cdot 2HCl$:
C, 59.53; H, 6.59; N, 6.31; Cl, 23.97.

Found: C, 59.36; H, 6.54; N, 6.57; Cl, 23.34; $H_2O$, 0.8.

Corrected for $H_2O$: C, 59.84; H, 6.50; N, 6.62; Cl, 23.53.

EXAMPLE 14

7-Chloro-4-[2-(4-methylpiperazino)ethyl]-5-phenyl-2,3,4,5-tetrahydro-1,4-benzoxazepine trihydrochloride The product of Example 10 (in free base form) was reduced with $LiAlH_4$ in diethyl ether by the general procedure of Example 5. The trihydrochloride salt was prepared and recrystallized from acetonitrile; 33.3% yield; mp 206°–210° C.

Anal. Calculated for $C_{22}H_{28}ClN_3O \cdot 3HCl$:
C, 53.34; H, 6.31; N, 8.45; Cl, 28.63.

Found: C, 51.69; H, 6.19; N, 8.34; Cl, 27.02; $H_2O$, 3.18.

Corrected for $H_2O$: C, 53.39; H, 6.03; N, 8.61; Cl, 27.91.

EXAMPLE 15

The general procedure of Example 1 is repeated except that the 5-chloro-2-hydroxybenzophenone utilized therein is replaced by an equimolar amount of
5-bromo-2-hydroxybenzophenone,
5-iodo-2-hydroxybenzophenone,
5-fluoro-2-hydroxybenzophenone,
5-nitro-2-hydroxybenzophenone,
5-trifluoromethyl-2-hydroxybenzophenone,
5,4'-dichloro-2-hydroxybenzophenone,
5-chloro-2'-fluoro-2-hydroxybenzophenone,
4'-chloro-2-hydroxybenzophenone,
2'-fluoro-2-hydroxybenzophenone,
5-nitro-4'-chloro-2-hydroxybenzophenone,
5-nitro-2'-fluoro-2-hydroxybenzophenone,
5-trifluoromethyl-4'-chloro-2-hydroxybenzophenone,
5-trifluoromethyl-2'-fluoro-2-hydroxybenzophenone,
5-bromo-4'-chloro-2-hydroxybenzophenone and
5-fluoro-4'-chloro-2-hydroxybenzophenone, respectively,
and there is thereby obtained
5-bromo-2-(2-chloroethoxy)benzophenone,
5-iodo-2-(2-chloroethoxy)benzophenone,
5-fluoro-2-(2-chloroethoxy)benzophenone,
5-nitro-2-(2-chloroethoxy)benzophenone,
5-trifluoromethyl-2-(2-chloroethoxy)benzophenone,
5,4'-dichloro-2-(2-chloroethoxy)benzophenone,
5-chloro-2'-fluoro-2-(2-chloroethoxy)benzophenone,
4'-chloro-2-(2-chloroethoxy)benzophenone,
2'-fluoro-2-(2-chloroethoxy)benzophenone,
5-nitro-4'-chloro-2-(2-chloroethoxy)benzophenone,
5-nitro-2'-fluoro-2-(2-chloroethoxy)benzophenone,
5-trifluoromethyl-4'-chloro-2-(2-chloroethoxy)benzophenone,
5-trifluoromethyl-2'-fluoro-2-(2-chloroethoxy)benzophenone,
5-bromo-4'-chloro-2-(2-chloroethoxy)benzophenone and
5-fluoro-4'-chloro-2-(2-chloroethoxy)benzophenone, respectively.

EXAMPLE 16

The general procedure of Example 2 is repeated except that the 5-chloro-2-(2-chloroethoxy)benzophenone utilized therein is replaced by an equimolar amount of
5-bromo-2-(2-chloroethoxy)benzophenone,
5-iodo-2-(2-chloroethoxy)benzophenone,
5-fluoro-2-(2-chloroethoxy)benzophenone,
5-nitro-2-(2-chloroethoxy)benzophenone,
5-trifluoromethyl-2-(2-chloroethoxy)benzophenone,
5,4'-dichloro-2-(2-chloroethoxy)benzophenone,
5-chloro-2'-fluoro-2-(2-choroethoxy)benzophenone,
4'-chloro-2-(2-chloroethoxy)benzophenone,
2'-fluoro-2-(2-chloroethoxy)benzophenone,
5-nitro-4'-chloro-2-(2-chloroethoxy)benzophenone,
5-nitro-2'-fluoro-2-(2-chloroethoxy)benzophenone,
5-trifluoromethyl-4'-chloro-2-(2-chloroethoxy)benzophenone,
5-trifluoromethyl-2'-fluoro-2-(2-chloroethoxy)benzophenone,
5-bromo-4'-chloro-2-(2-chloroethoxy)benzophenone and
5-fluoro-4'-chloro-2-(2-chloroethoxy)benzophenone, respectively, and there is thereby obtained
5-bromo-2-(2N-phthalimidoethoxy)benzophenone,
5-iodo-2-(2N-phthalimidoethoxy)benzophenone,
5-fluoro-2-(2N-phthalimidoethoxy)benzophenone,
5-nitro-2-(2N-phthalimidoethoxy)benzophenone,
5-trifluoromethyl-2-(2N-phthalimidoethoxy)benzophenone,
5,4'-dichloro-2-(2N-phthalimidoethoxy)benzophenone,
5-chloro-2'-fluoro-2-(2N-phthalimidoethoxy)benzophenone,
4'-chloro-2-(2N-phthalimidoethoxy)benzophenone,
2'-fluoro-2-(2-N-phthalimidoethoxy)benzophenone,
5-nitro-4'-chloro-2-(2N-phthalimidoethoxy)benzophenone,
5-nitro-2'-fluoro-2-(2N-phthalimidoethoxy)benzophenone,
5-trifluoromethyl-4'-chloro-2-(2N-phthalimidoethoxy)benzophenone,
5-trifluoromethyl-2'-fluoro-2-(2N-phthalimidoethoxy)benzophenone,
5-bromo-4'-chloro-2-(2N-phthalimidoethoxy)benzophenone and
5-fluoro-4'-chloro-2-(2N-phthalimidoethoxy)benzophenone, respectively.

EXAMPLE 17

The general procedure of Example 3 is repeated except that the 5-chloro-2-(2N-phthalimidoethoxy)benzophenone utilized therein is replaced by an equimolar amount of
5-bromo-2-(2-N-phthalimidoethoxy)benzophenone,
5-iodo-2-(2-N-phthalimidoethoxy)benzophenone,
5-fluoro-2-(2-N-phthalimidoethoxy)benzophenone, 5-trifluoromethyl-2-(2-N-phtolimidoethoxy)benzophenone, 5,4'-dichloro-2-(2-N-phthalimidoethoxy)benzophenone, 5-chloro-2'-fluoro-2-(2-N-phthalimidoethoxy)benzophenone, 4'-chloro-2-(2-N-phthalimidoethoxy)benzophenone, 2'-fluoro-2-(2-N-phthalimidoethoxy)benzophenone, 5-trifluoromethyl-4'-chloro-2-(2-N-phthalimidoethoxy)benzophenone, 5-trifluoromethyl-2'-fluoro-2-(2-N-phthalimidoethoxy)benzophenone, 5-bromo-4'-chloro-2-(2-N-phthalimidoethoxy)benzophenone and 5-fluoro-4'-chloro-2-(2-N-phthalimidoethoxy)benzophenone, respectively, and there is thereby obtained 7-bromo-5-phenyl-2,3,4,5-tetrahydro-1,4-benzoxazepine hydrochloride, 7-iodo-5-phenyl-2,3,4,5-tetrahydro-1,4-benzoxazepine hydrochloride, 7-fluoro-5-phenyl-2,3,4,5-tetrahydro-1,4-benzoxazepine hydrochloride, 7-trifluoromethyl-5-phenyl-2,3,4,5-tetrahydro-1,4-benzoxazepine hydrochloride, 7-chloro-5-(4-chlorophenyl)-2,3,4,5-tetrahydro-1,4-benzoxazepine hydrochloride, 7-chloro-5-(2-fluorophenyl)-2,3,4,5-tetrahydro-1,4-benzoxazepine hydrochloride, 5-(4-chlorophenyl)-2,3,4,5-tetrahydro-1,4-benzoxazepine hydrochloride, 5-(2-fluorophenyl)-2,3,4,5-tetrahydro-1,4,-benzoxazepine hydrochloride, 7-trifluoromethyl-5-(4-chlorophenyl)-2,3,4,5:tetrahydro-1,4-benzoxazepine hydrochloride, 7-trifluoromethyl-5-(2-fluorophenyl)-2,3,4,5-tetrahydro-1,4-benzoxazepine hydrochloride, 7-bromo-5-(4-chlorophenyl)-2,3,4,5-tetrahydro-1,4-benzoxazepine hydrochloride and 7-fluoro-5-(4-chlorophenyl)-2,3,4,5-tetrahydro-1,4-benzoxazepine hydrochloride, respectively.

EXAMPLE 18

The general procedure of Example 3, steps (a) and (b) are repeated except that the 5-chloro-2-(2-N-phthalimidoethoxy) benzophenone utilized therein is replaced by an equimolar amount of 5-nitro-2-(2-N-phthalimidoethoxy)benzophenone, 5-nitro-4'-chloro-2-(2-N-phthalimidoethoxy)benzophenone and 5-nitro-2'-fluoro-2-(2-N-phthalimidoethoxy)benzophenone, respectively, and there is thereby obtained 7-nitro-5-phenyl-2,3-dihydro-1,4-benzoxazepine hydrochloride, 7-nitro-5-(4-chlorophenyl)-2,3-dihydro-1,4-benzoxazepine hydrochloride and 7-nitro-5-(2-fluorophenyl)-2,3-dihydro-1,4-benzoxazepine hydrochloride, respectively.

These three dihydro compounds cannot be reduced to the corresponding tetrahydro compounds by the general procedure of Example 3, step (c), i.e. by the use of LiAlH$_4$, without the concomitant reduction of the nitro substituents. They are, however, successfully reduced to the corresponding tetrahydro compounds, without reduction of the nitro substituents, by the use of diborane in tetrahydrofuran. A general procedure for reduction with diborane is described in Example 4, step (c), being used there for the reduction of an amide. The general procedure of Example 4, step (c) is repeated except that the 7-chloro-4-(2-dimethylaminoacetyl)-5-phenyl-2,3,4,5-tetrahydro-1,4-benzoxazepine is replaced by the three above-produced dihydro compounds, respectively, and there is thereby obtained 7-nitro-5-phenyl-2,3,4,5-tetrahydro-1,4-benzoxazepine hydrochloride, 7-nitro-5-(4-chlorophenyl)-2,3,4,5-tetrahydro-1,4-benzoxazepine hydrochloride and 7-nitro-5-(2-fluorophenyl)-2,3,4,5-tetrahydro-1,4-benzoxazepine hydrochloride, respectively.

EXAMPLE 19

The general procedure of Example 4 is repeated except that the 7-chloro-5-phenyl-2,3,4,5-tetrahydro-1,4-benzoxazepine hydrochloride utilized therein is replaced by an equimolar amount of 7-bromo-5-phenyl-2,3,4,5-tetrahydro-1,4-benzoxazepine hydrochloride, 7-iodo-5-phenyl-2,3,4,5-tetrahydro-1,4-benzoxazepine hydrochloride, 7-fluoro-5-phenyl-2,3,4,5-tetrahydro-1,4-benzoxazepine hydrochloride, 7-nitro-5-phenyl-2,3,4,5-tetrahydro-1,4-benzoxazepine hydrochloride, 7-trifluoromethyl-5-phenyl-2,3,4,5-tetrahydro-1,4-benzoxazepine hydrochloride, 7-chloro-5-(4-chlorophenyl)-2,3,4,5-tetrahydro-1,4-benzoxazepine hydrochloride, 7-chloro-5-(2-fluorophenyl)-2,3,4,5-tetrahydro-1,4-benzoxazepine hydrochloride, 5-(4-chlorophenyl)-2,3,4,5-tetrahydro-1,4-benzoxazepine hydrochloride, 5-(2-fluorophenyl)-2,3,4,5-tetrahydro-1,4-benzoxazepine hydrochloride, 7-nitro-5-(4-chlorophenyl)-2,3,4,5-tetrahydro-1,4-benzoxazepine hydrochloride, 7-nitro-5-(2-fluorophenyl)-2,3,4,5-tetrahydro-1,4-benzoxazepine hydrochloride, 7-trifluoromethyl-5-(4-chlorophenyl)-2,3,4,5-tetrahydro-1,4-benzoxazepine hydrochloride, 7-trifluoromethyl-5-(2-fluorophenyl)-2,3,4,5-tetrahydro-1,4-benzoxazepine hydrochloride, 7-bromo-5-(4-chlorophenyl-2,3,4,5-tetrahydro-1,4-benzoxazepine hydrochloride and 7-fluoro-5-(4-chlorophenyl)-2,3,4,5-tetrahydro-1,4-benzoxazepine hydrochloride, respectively, and there is thereby obtained 7-bromo-5-phenyl-4-(2-dimethylaminoethyl)-2,3,4,5-tetrahydro-1,4-benzoxazepine dihydrochloride 7-iodo-5-phenyl-4-(2-dimethylaminoethyl)-2,3,4,5-tetrahydro-1,4-benzoxazepine dihydrochloride, 7-fluoro-5-phenyl-4-(2-dimethylaminoethyl)-2,3,4,5-tetrahydro-1,4-benzoxazepine dihydrochloride, 7-nitro-5-phenyl-4-(2-dimethylaminoethyl)-2,3,4,5-tetrahydro-1,4-benzoxazepine dihydrochloride, 7-trifluoromethyl-5-phenyl-4-(2-dimethylaminoethyl)-2,3-4,5-tetrahydro-1,4-benzoxazepine dihydrochloride, 7-chloro-5-(4-chlorophenyl)-4-(2-dimethylaminoethyl)-2,3,4,5-tetrahydro-1,4-benzoxazepine dihydrochloride, 7-chloro-5-(2-fluorophenyl)-4-(2-dimethylaminoethyl)-2,3,4,5-tetrahydro-1,4-benzoxazepine dihydrochloride, 5-(4-chlorophenyl)-4-(2-dimethylaminoethyl)-2,3,4,5-tetrahydro-1,4-benzoxazepine dihydrochloride, 5-(2-fluorophenyl)-4-(2-dimethylaminoethyl)-2,3,4,5-tetrahydro-1,4-benzoxazepine dihydrochloride, 7-nitro-5-(4-chlorophenyl)-4-(2-dimethylaminoethyl)-2,3,4,5-tetrahydro-1,4-benzoxazepine dihydrochloride, 7-nitro-5-(2-fluorophenyl)-4-(2-dimethylaminoethyl)-2,3,4,5-tetrahydro-1,4-benzoxazepine dihydrochloride, 7-trifluoromethyl-5-(4-chlorophenyl)-4-(2-dimethylaminoethyl)-2,3,4,5-tetrahydro-1,4-benzoxazepine dihydrochloride, 7-trifluoromethyl-5-(2-fluorophenyl)-4-(2-dimethylaminoethyl)-2,3,4,5-tetrahydro-1,4-benzoxazepine dihydrochloride, 7-bromo-5-(4-chlorophenyl)-4-(2-dimethylaminoethyl)-2,3,4,5-tetrahydro-1,4-benzoxazepine dihydrochloride and 7-fluoro-5-(4-chlorophenyl)-4-(2-dimethylaminoethyl)-2,3,4,5-tetrahydro-1,4-benzoxazepine dihydrochloride, respectively.

EXAMPLE 20

The general procedure of Example 7 is repeated except that the 7-chloro-4-(2-chloroacetyl)-5-phenyl-2,3,4,5-tetrahydro-1,4-benzoxazepine utilized therein is replaced by an equimolar amount of 7-bromo-5-phenyl-4-(2-chloroacetyl)-2,3,4,5-tetrahydro-1,4-benzoxazepine, 7-iodo-5-phenyl-4-(2-chloroacetyl)-2,3,4,5-tetrahydro-1,4-benzoxazepine, 7-fluoro-5-phenyl-4-(2-chloroacetyl)-2,3,4,5-tetrahydro-1,4-benzoxazepine, 7-nitro-5-phenyl-4-(2-chloroacetyl)-2,3,4,5-tetrahydro-1,4-benzoxazepine, 7-trifluoromethyl-5-phenyl-4-(2-chloroacetyl)-2,3,4,5-tetrahydro-1,4-benzoxazepine, 7-chloro-5-(4-chlorophenyl)-4-(2-chloroacetyl)-2,3,4,5-tetrahydro-1,4-benzoxazepine, 7-chloro-5-(2-fluorophenyl)-4-(2-chloroacetyl)-2,3,4,5-tetrahydro-1,4,-benzoxazepine, 5-(4-chlorophenyl)-4-(2-chloroacetyl)-2,3,4,5-tetrahydro-1,4,-benzoxazepine, 5-(2-fluorophenyl)-4-(2-chloroacetyl)-2,3,4,5-tetrahydro-1,4,-benzoxazepine, 7-nitro-5-(4-chlorophenyl)-4-(2-chloroacetyl)-2,3,4,5-tetrahydro-1,4-benzoxazepine, 7-nitro-5(2-fluorophenyl)-4-(2-chloroacetyl)-2,3,4,5-tetrahydro-1,4-benzoxazepine, 7-trifluoromethyl-5-(4-chlorophenyl)-4-(2-chloroacetyl)-2,3,4,5-tetrahydro-1,4,-benzoxazepine, 7-trifluoromethyl-5-(2-fluorophenyl)-4-(2-chloroacetyl)-2,3,4,5-tetrahydro-1,4,-benzoxazepine, 7-bromo-5-(4-chlorophenyl)-4-(2-chloroacetyl)-2,3,4,5-tetrahydro-1,4-benzoxazepine and 7-fluoro-5-(4-chlorophenyl)-4-(2-chloroacetyl)-2,3,4,5-tetrahydro-1,4-benzoxazepine, respectively, and the resulting 4-(1-oxo-2-pyrrolidinoethyl) intermediate compounds are reduced with diborane in tetrahydrofuran by the general procedure of Example 4, step (c). There is thereby obtained 7-bromo-5-phenyl-4(2-pyrrolidinoethyl)-2,3,4,5-tetrahydro-1,4,-benzoxazepine dihydrochloride, 7-iodo-5-phenyl-4-(2-pyrrolidinoethyl)-2,3,4,5-tetrahydro-1,4,-benzoxazepine dihydrochloride, 7-fluoro-5-phenyl-4-(2-pyrrolidinoethyl)-2,3,4,5-tetrahydro-1,4-benzoxazepine dihydrochloride, 7-nitro-5-phenyl-4-(2-pyrrolidinoethyl)-2,3,4,5-tetrahydro-1,4,-benzoxazepine dihydrochloride, 7-trifluoromethyl-5-phenyl-4-(2-pyrrolidinoethyl)-2,3,4,5-tetrahydro-1,4-benzoxazepine dihydrochloride, 7-chloro-5-(4-chlorophenyl)-4-(2-pyrrolidinoethyl)-2,3,4,5-tetrahydro-1,4-benzoxazepine dihydrochloride, 7-chloro-5-(2-fluorophenyl)-4-(2-pyrrolidinoethyl)-2,3,4,5-tetrahydro-1,4-benzoxazepine dihydrochloride, 5-(4-chlorophenyl)-4-(2-pyrrolidinoethyl)-2,3,4,5-tetrahydro-1,4-benzoxazepine dihydrochloride, 5-(2-fluorophenyl)-4-(2-pyrrolidinoethyl)-2,3,4,5-tetrahydro-1,4-benzoxazepine dihydrochloride, 7-nitro-5-(4-chlorophenyl)-4-(2-pyrrolidinoethyl)-2,3,4,5-tetrahydro-1,4-benzoxazepine dihydrochloride, 7-nitro-5-(2-fluorophenyl)-4-(2-pyrrolidinoethyl)-2,3,4,5-tetrahydro-1,4-benzoxazepine dihydrochloride, 7-trifluoromethyl-5-(4-chlorophenyl)-4-(2-pyrrolidinoethyl)-2,3,4,5-tetrahydro-1,4-benzoxazepine dihydrochloride, 7-trifluoromethyl-5-(2-fluorophenyl)-4-(2-pyrrolidinoethyl)-2,3,4,5-tetrahydro-1,4-benzoxazepine dihydrochloride, 7-bromo-5-(4-chlorophenyl)-4-(2-pyrrolidinoethyl)-2,3,4,5-tetrahydro-1,4-benzoxazepine dihydrochloride and 7-fluoro-5-(4-chlorophenyl)-4-(2-pyrrolidinoethyl)-2,3,4,5-tetrahydro-1,4-benzoxazepine dihydrochloride, respectively.

EXAMPLE 21

7-Chloro-4-(4-dimethylaminobutyl)-5-phenyl-2,3,4,5-tetrahydro-1,4-benzoxazepine dihydrochloride The general procedure of Example 4 is repeated except that the chloroacetyl chloride utilized therein is replaced by an equimolar amount of 4-chloro-n-butyryl chloride and there is thereby obtained 7-chloro-4-(4-dimethylaminobutyl)-5-phenyl-2,3,4,5-tetrahydro-1,4-benzoxazepine dihydrochloride.

I claim:

1. A compound having the formula

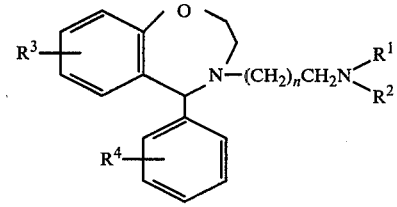

wherein

R$^1$ and R$^2$ each represent methyl or, when taken together with the nitrogen to which they are attached, represent pyrrolidino, R$^3$ and R$^4$ are the same or different and represent hydrogen, chloro, fluoro, bromo, iodo, nitro (lower)alkyl, trifluoromethyl, (lower)alkoxy, trifluoromethoxy or (lower)alkylthio, and n is an integer from 1 to 4, or a nontoxic, pharmaceutically acceptable acid addition salt thereof.

2. A compound of claim 1 having the formula

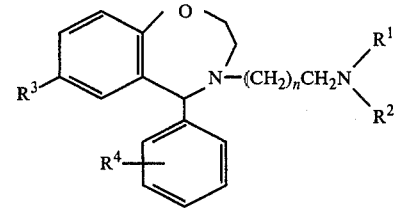

wherein R¹ and R² each represent methyl or, when taken together with the nitrogen to which they are attached, represent pyrrolidino, n is an integer from 1 to 4, and R³ and R⁴ are the same or different and represent hydrogen, chloro, fluoro, bromo, iodo, nitro or trifluoromethyl, or a nontoxic, pharmaceutically acceptable acid addition salt thereof.

3. A compound of claim 2 in which R⁴ is hydrogen, 4-chloro or 2-fluoro, or a nontoxic, pharmaceutically acceptable acid addition salt thereof.

4. A compound of the formula

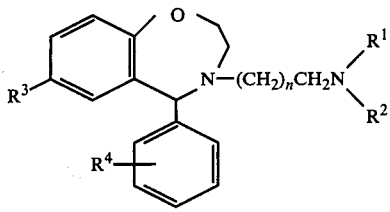

wherein R¹ and R² each represent methyl or, when taken together with the nitrogen to which they are attached, represent pyrrolidino, R³ is hydrogen, chloro, fluoro, bromo, iodo, nitro or trifluoromethyl, and n is an integer from 1 to 4, or a nontoxic, pharmaceutically acceptable acid addition salt thereof.

5. A compound of claim 4 in which R³ is chloro, or a nontoxic, pharmaceutically acceptable acid addition salt thereof.

6. A compound of claim 5 in which n is 1, or a nontoxic pharmaceutically acceptable acid addition salt thereof.

7. 7-Chloro-4(2-dimethylaminoethyl)-5-phenyl-2,3,4,5-tetrahydro-1,4-benzoxazepine, or a nontoxic, pharmaceutically acceptable acid addition salt thereof.

8. The dihydrochloride of the compound of claim 7.

9. The d- or l-isomer of a compound of claim 7.

10. The dihydrochloride of a compound of claim 9.

11. 7-Chloro-4-(2-pyrrolidinoethyl)-5-phenyl-2,3,4,5-tetrahydro-1,4-benzoxazepine, or a nontoxic, pharmaceutically acceptable acid addition salt thereof.

12. The dihydrochloride of the compound of claim 11.

13. The d- or l-isomer of a compound of claim 11.

14. The dihydrochloride of a compound of claim 13.

* * * * *

UNITED STATES PATENT AND TRADEMARK OFFICE
CERTIFICATE OF CORRECTION

PATENT NO. : 4,125,538
DATED : November 14, 1978
INVENTOR(S) : Robert T. Standridge It is certified that error appears in the above-identified patent and that said Letters Patent are hereby corrected as shown below:

In column 1, the right-hand structural formula should be:

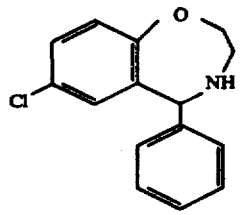

In claim 4, $R^4$ should be deleted from the structural formula.

Claim 7 should read:

"7-Chloro-4-(2-dimethylaminoethyl)-5-phenyl-2,3,4,5-tetrahydro-1,4-benzoxazepine, or a nontoxic, pharmaceutically acceptable acid addition salt thereof."

Signed and Sealed this

Thirteenth Day of March 1979

[SEAL]

Attest:

RUTH C. MASON
Attesting Officer

DONALD W. BANNER
Commissioner of Patents and Trademarks